(12) United States Patent
Stork et al.

(10) Patent No.: US 9,139,549 B2
(45) Date of Patent: Sep. 22, 2015

(54) PROCESS FOR THE INTEGRATED PREPARATION OF 2-SUBSTITUTED 4-HYDROXY-4-METHYLTETRA HYDROPYRANS AND OF 2-SUBSTITUTED 4-METHYLTETRAHYDROPYRANS

(71) Applicant: BASF SE, Ludwigshafen (DE)

(72) Inventors: Timon Stork, Mannheim (DE); Oskar Röder, Gommersheim (DE); Klaus Ebel, Heddesheim (DE); Ralf Pelzer, Fürstenberg (DE); Wolfgang Krause, Brühl-Rohrhof (DE); Karl Beck, Östringen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/053,020

(22) Filed: Oct. 14, 2013

(65) Prior Publication Data
US 2014/0107352 A1    Apr. 17, 2014

Related U.S. Application Data

(60) Provisional application No. 61/713,656, filed on Oct. 15, 2012.

(51) Int. Cl.
*C07D 309/04* (2006.01)
*C07D 309/10* (2006.01)

(52) U.S. Cl.
CPC ............ *C07D 309/10* (2013.01); *C07D 309/04* (2013.01)

(58) Field of Classification Search
CPC ........................... C07D 309/04; C07D 309/10
USPC ................................................. 549/356, 416
See application file for complete search history.

(56) References Cited

U.S. PATENT DOCUMENTS

| | | | |
|---|---|---|---|
| 2,471,134 A | 5/1949 | Wright | |
| 8,618,315 B2 * | 12/2013 | Gralla et al. | 549/423 |
| 2011/0295024 A1 * | 12/2011 | Gralla et al. | 549/416 |
| 2012/0059177 A1 | 3/2012 | Gralla et al. | |

FOREIGN PATENT DOCUMENTS

| | | |
|---|---|---|
| EP | 0 122 367 A2 | 10/1984 |
| EP | 1493737 A1 | 1/2005 |
| EP | 1516879 A1 | 3/2005 |
| EP | 1927593 A1 * | 6/2008 |
| WO | WO-2010133473 A1 | 11/2010 |
| WO | WO-2011/147919 A1 | 12/2011 |
| WO | WO-2011154330 A1 | 12/2011 |

OTHER PUBLICATIONS

Tyman, J.H.P., et al., "The Reaction of 3-Alkene-1-Ols with Aldehydes: A Synthesis of (+/−)-Cis-2-(2'Methyl-1'-Propenyl)-4-Methyltetrahydropyran", Tetrahedron Letters, No. 51, (1970), pp. 4507-4508.
Julia, Par Marc, et al., "Sythèse de l'oxyde Rose et de Composes Voisins", Bulletin de la Societe Chimique de France 1963, (1983), pp. 8-9.
English translation of International Preliminary Report on Patentability for PCT/EP2013/071409 dated Sep. 5, 2014.

* cited by examiner

*Primary Examiner* — Noble Jarrell
*Assistant Examiner* — John Mauro
(74) *Attorney, Agent, or Firm* — Drinker Biddle & Reath LLP

(57) ABSTRACT

The present invention relates to a process for the integrated preparation of 2-substituted 4-hydroxy-4-methyltetrahydropyrans and of 2-substituted 4-methyltetrahydropyrans.

21 Claims, No Drawings

PROCESS FOR THE INTEGRATED PREPARATION OF 2-SUBSTITUTED 4-HYDROXY-4-METHYLTETRAHYDROPYRANS AND OF 2-SUBSTITUTED 4-METHYLTETRAHYDROPYRANS

CROSS-REFERENCE TO RELATED APPLICATIONS

This Application claims the benefit of U.S. Provisional Application 61/713,656 filed on Oct. 15, 2012 which is incorporated by reference.

BACKGROUND OF THE INVENTION

The present invention relates to a process for the integrated preparation of 2-substituted 4-hydroxy-4-methyltetrahydropyrans and of 2-substituted 4-methyltetrahydropyrans.

PRIOR ART

2-Substituted 4-hydroxy-4-methyltetrahydropyrans are valuable compounds for use as aroma chemicals. Thus, for example, the cis/trans-diastereomer mixture of 2-(2-methylpropyl)-4-hydroxy-4-methyltetrahydropyran

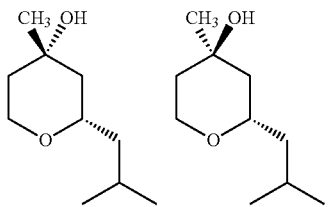

is characterized by a pleasant lily of the valley scent and is suitable to a particular extent to use as an aroma chemical, e.g. for producing fragrance compositions.

EP 1 493 737 A1 discloses a process for preparing mixtures of ethylenically unsaturated 4-methyl- and 4-methylenepyrans and the corresponding 4-hydroxypyrans by reacting the corresponding aldehydes with isoprenol, the reaction being initiated in a reaction system in which the molar ratio of aldehyde to isoprenol is greater than 1, i.e. the aldehyde is used in excess. Moreover, the document discloses the subsequent dehydration of said mixtures to give the desired ethylenically unsaturated pyrans. Suitable catalysts given for the first reaction step are mineral acids such as hydrochloric acid or sulfuric acid, but preferably methanesulfonic acid or p-toluenesulfonic acid.

EP 1 516 879 A1 discloses a process for preparing ethylenically unsaturated 4-methyl- and 4-methylenepyrans by reacting a corresponding aldehyde with isoprenol under dehydrating conditions, where the amount of water in the reactor is up to 0.25% by weight, while the conversion of the starting compound used in deficit is less than 50%. Suitable catalysts for this purpose that are given are likewise mineral acids such as hydrochloric acid or sulfuric acid, but preferably methanesulfonic acid or p-toluenesulfonic acid.

WO 2010/133473 describes a process for preparing 2-substituted 4-hydroxy-4-methyltetrahydropyrans of the formula (I)

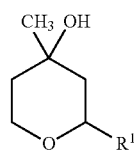

(I)

where the radical $R^1$ is a straight-chain or branched alkyl or alkenyl radical having 1 to 12 carbon atoms, an optionally alkyl-substituted cycloalkyl radical having in total 3 to 12 carbon atoms and an optionally alkyl- and/or alkoxy-substituted aryl radical having in total 6 to 12 carbon atoms, in which isoprenol (3-methylbut-3-en-1-ol) is reacted with an aldehyde of the formula $R^1$—CHO, where the reaction is carried out in the presence of water and in the presence of a strongly acidic cation exchanger.

WO 2011/154330 describes a process comparable to WO 2010/133473, where the reaction mixture obtained is carried out a distillative work-up in a dividing-wall column or in two thermally coupled distillation columns.

As described in WO 2010/133473 and WO 2011/154330, in the acid-catalyzed reaction of isoprenol (3-methylbut-3-en-1-ol) with an aldehyde of the formula $R^1$—CHO, a complex reaction mixture is produced which, besides 2-substituted 4-hydroxy-4-methyltetrahydropyrans, also comprises dehydrated by-products of the formulae (A), (B) and/or (C)

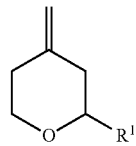

(A)

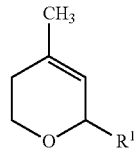

(B)

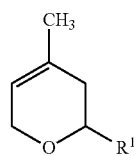

(C)

and, as further by-products, acetals (D) and 1,3-dioxanes (E)

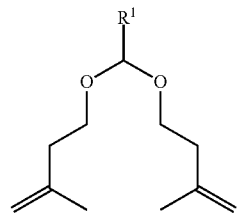

(D)

-continued (E)

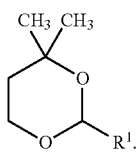

These by-products have hitherto been unable to be utilized for providing further valuable substances, but are either removed from the system or returned again to the reaction of isoprenol with the aldehyde together with the starting compounds used in excess. The latter is not without problems on account of a possible buildup in the level of these components in the reaction mixture.

WO 2011/147919 describes a process for preparing 2-substituted 4-hydroxy-4-methyltetrahydropyranols and specifically 2-isobutyl-4-hydroxy-4-methyltetrahydropyran by reacting isoprenol with prenal and subsequent hydrogenation.

A further valuable aroma chemical is 2-(2-methylpropyl)-4-methyltetrahydro-2H-pyran, which is also referred to as dihydrorose oxide.

Dihydrorose oxide was isolated for the first time from Bulgarian rose oil and then prepared synthetically by Julia and Jacquet (Julia, M.; Jacquet, B., Bulletin de la Societe Chimique de France 1963, 8-9, 1983). A cyclic acetal was obtained starting from but-2-en-1-al by means of a Diels-Alder reaction with ethyl vinyl ether and subsequent hydrogenation. After cleaving off of ethanol, hydrobromination of the resulting double bond and concluding Grignard reaction with isopropylmagnesium bromide, the mixture of cis- and trans-dihydrorose oxide was able to be prepared synthetically for the first time.

J. H. P. Tyman and B. J. Willis describe in Tetrahedron Letters No. 51, 4507-4508, 1970, the acid-catalyzed reaction of 3-alken-1-ols with aldehydes, specifically the reaction of 3-methyl-2-buten-1-al with 2-methyl-1-buten-4-ol and subsequent dehydration. The intermediate having an exocyclic methylene group obtained in this way was hydrogenated under homogeneous catalysis in the presence of $SnCl_2$/$H_2PtCl_6$ to give racemic cis-2-(2-methylprop-1-en-yl)-4-methyltetrahydropyran.

It is the object of the present invention to provide an improved process for preparing 2-substituted 4-hydroxy-4-methyltetrahydropyrans which also permits the greatest possible effective utilization of the hitherto unusable by-products.

Surprisingly, it has now been found that the by-product-containing side stream (=waste stream) that is produced during the acid-catalyzed preparation of 2-substituted 4-hydroxy-4-methyltetrahydropyrans by reacting isoprenol (3-methylbut-3-en-1-ol) with a suitable aldehyde is suitable for preparing 2-substituted 4-methyltetrahydropyrans and specifically for preparing dihydrorose oxide. Here, it is particularly problematic that the main components of the side stream, the three isomeric dihydropyranols (A), (B) and (C) on the one hand and the dioxane (E) on the other hand cannot be separated by distillation with justifiable expenditure. Surprisingly, however, it has been found that by hydrogenating the entire side stream the isomeric dihydropyranols (A), (B) and (C) can be converted to 2-substituted 4-methyltetrahydropyrans which can then be removed by distillation from the unusable dioxane (E). An integrated process for the simultaneous preparation of 2-substituted 4-hydroxy-4-methyltetrahydropyrans and of 2-substituted 4-methyltetrahydropyrans is thus provided. A large part of the previous side stream can thus also be provided for the use as aroma chemical and specifically as fragrance.

SUMMARY OF THE INVENTION

The invention firstly provides a process for preparing 2-substituted 4-hydroxy-4-methyltetrahydropyrans of the general formula (I) and of 2-substituted 4-methyltetrahydropyrans of the general formula (II)

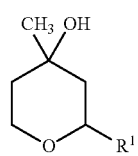

(I)

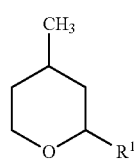

(II)

in which
R$^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms, in which
a) 3-methylbut-3-en-1-ol of the formula (III)

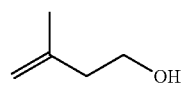

(III)

is reacted with an aldehyde of the formula (IV)

 (IV)

where R$^1$ in the formula (IV) has the meaning given above, in the presence of an acidic catalyst, giving a reaction mixture which comprises at least one 2-substituted 4-hydroxy-4-methyltetrahydropyran of the general formula (I), at least one of the compounds (V.1), (V.2) or (V.3) and at least one dioxane compound (VI)

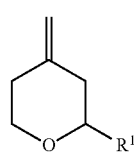

(V.1)

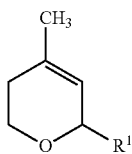

(V.2)

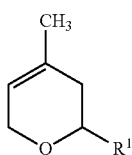

(V.3)

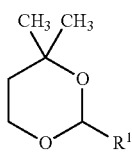

(VI)

where R¹ in the formula (VI) has the meaning given above, b) the reaction product from step a) is subjected to a separation, giving a fraction enriched in 2-substituted 4-hydroxy-4-methyltetrahydropyrans of the general formula (I) and a fraction which comprises at least one of the compounds (V.1), (V.2) or (V.3) and at least one dioxane compound (VI), c) the fraction which comprises at least one of the compounds (V.1), (V.2) or (V.3) and at least one dioxane compound (VI) is subjected to a hydrogenation, d) a fraction enriched in 2-substituted 4-methyltetrahydropyrans (II) and a fraction enriched in the at least one dioxane compound (VI) are isolated from the hydrogenation product obtained in step c).

DESCRIPTION OF THE INVENTION

The process according to the invention has the following advantages:

a large part of the previous side stream (waste stream) during the acid-catalyzed preparation of 2-substituted 4-hydroxy-4-methyltetrahydropyrans can be used as a product of value.

The hydrogenation envisaged according to the invention allows access to 2-substituted 4-methyltetrahydropyrans and specifically to dihydrorose oxide, which requires only one reaction stage, starting from the side stream.

The unusable dioxanes present in the reaction mixture for preparing 2-substituted 4-hydroxy-4-methyltetrahydropyrans can be effectively separated off from the product of value after the hydrogenation.

To prepare the 2-substituted 4-methyltetrahydropyrans, specifically dihydrorose oxide, it is not necessary to use any further expensive and/or potentially hazardous reagents, such as for example Grignard reagents or complex hydrides, such as lithium aluminum hydride.

Unless stated more precisely hereinbelow, the terms
"2-substituted 4-hydroxy-4-methyltetrahydropyran",
"2-substituted 4-methyltetrahydropyran",
"2-(2-methylpropyl)-4-hydroxy-4-methyltetrahydropyran",
"2-(2-methylpropyl)-4-methyltetrahydropyran" (="dihydrorose oxide"), refer within the context of the invention to cis/trans mixtures of any composition and also to the pure conformational isomers. The terms specified above also refer to all enantiomers in pure form and also to racemic and optically active mixtures of the enantiomers of these compounds.

If cis and trans diastereomers of the compounds (I) or (II) are discussed hereinbelow, only one of enantiomeric forms is depicted in each case. The isomers of 2-(2-methylpropyl)-4-methyltetrahydropyran (II) (dihydrorose oxide) are reproduced below merely for the purposes of illustration:

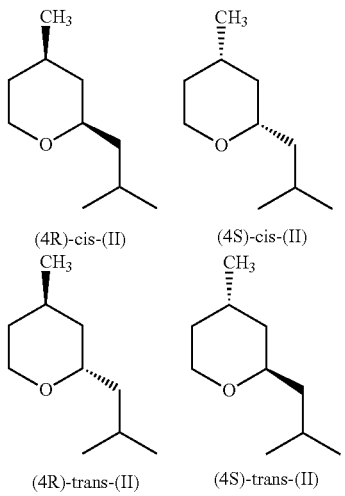

(4R)-cis-(II)   (4S)-cis-(II)

(4R)-trans-(II)   (4S)-trans-(II)

Within the context of the present invention, the expression straight-chain or branched alkyl preferably stands for $C_1$-$C_6$-alkyl and particularly preferably for $C_1$-$C_4$-alkyl. Alkyl is in particular methyl, ethyl, n-propyl, isopropyl, n-butyl, isobutyl(2-methylpropyl), sec-butyl(1-methylpropyl), tert-butyl (1,1-dimethylethyl), n-pentyl or n-hexyl. Specifically, alkyl is methyl, ethyl, n-propyl, isopropyl or isobutyl.

Within the context of the present invention, the expression straight-chain or branched alkoxy preferably stands for $C_1$-$C_6$-alkoxy and particularly preferably for $C_1$-$C_4$-alkoxy. Alkoxy is in particular methoxy, ethoxy, n-propyloxy, isopropyloxy, n-butyloxy, isobutyloxy, sec-butyloxy, tert-butyloxy, n-pentyloxy or n-hexyloxy. Specifically, alkoxy is methoxy, ethoxy, n-propyloxy, isopropyloxy or isobutyloxy.

Within the context of the present invention, the expression straight-chain or branched alkenyl preferably stands for $C_2$-$C_6$-alkenyl and particularly preferably for $C_2$-$C_4$-alkenyl. Besides single bonds, the alkenyl radical also has one or more, preferably 1 to 3, particularly preferably 1 or 2 and very particularly preferably one, ethylenic double bond. Alkenyl is in particular ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

Within the context of the invention, cycloalkyl refers to a cycloaliphatic radical having preferably 3 to 10, particularly preferably 5 to 8, carbon atoms. Examples of cycloalkyl groups are in particular cyclopropyl, cyclobutyl, cyclopentyl, cyclohexyl, cycloheptyl or cyclooctyl. Specifically, cycloalkyl is cyclohexyl.

Substituted cycloalkyl groups can have one or more (e.g. 1, 2, 3, 4 or 5) substituents depending on the ring size. These are preferably selected, independently of one another, from $C_1$-$C_6$-alkyl and $C_1$-$C_6$-alkoxy. In the case of a substitution, the cycloalkyl groups preferably carry one or more, for example one, two, three, four or five, $C_1$-$C_6$-alkyl groups. Examples of substituted cycloalkyl groups are in particular 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl and 2-, 3- and 4-isobutylcyclohexyl.

Within the context of the present invention, the expression "aryl" comprises mono- or polynuclear aromatic hydrocarbon radicals having usually 6 to 18, preferably 6 to 14, particularly preferably 6 to 10, carbon atoms. Examples of aryl are in particular phenyl, naphthyl, indenyl, fluorenyl, anthracenyl, phenanthrenyl, naphthacenyl, chrysenyl, pyrenyl, etc., and specifically phenyl or naphthyl.

Substituted aryls can have one or more (e.g. 1, 2, 3, 4 or 5) substituents depending on the number and size of their ring systems. These are preferably selected, independently of one another, from $C_1$-$C_6$-alkyl and $C_1$-$C_6$-alkoxy. Examples of substituted aryl radicals are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl.

Step a)

One of the starting materials for step a) of the process according to the invention is 3-methylbut-3-en-1-ol (isoprenol) of the formula (III),

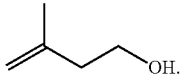

(III)

Isoprenol is readily accessible on any scale by known processes from isobutene and formaldehyde and is commercially available. No particular requirements are placed on the purity, grade or preparation procedure of the isoprenol to be used in accordance with the invention. It can be used in standard commercial grade and purity in step a) of the process according to the invention. Preference is given to using isoprenol which has a purity of 90% by weight or above, particularly preferably that with a purity of 95 to 100% by weight and very particularly preferably that with a purity of 97 to 99.9% by weight or even more preferably 98 to 99.8% by weight.

A further starting material for step a) of the process according to the invention is an aldehyde of the formula (IV) $R^1$—CHO, where $R^1$ in the formula (IV) has the meaning given above.

Preferably, $R^1$ in the compounds of the formula (I), (II), (IV), (V.1), (V.2), (V.3) and (VI) is a straight-chain or branched $C_1$-$C_{12}$-alkyl or straight-chain or branched $C_2$-$C_{12}$-alkenyl. Particularly preferably, $R^1$ is straight-chain or branched $C_1$-$C_6$-alkyl or straight-chain or branched $C_2$-$C_6$-alkenyl. In a further preferred embodiment, $R^1$ is phenyl.

Meanings preferred according to the invention for the radical $R^1$ are thus, for example, methyl, ethyl, n-propyl, isopropyl, n-butyl, isobutyl, n-pentyl, n-hexyl or n-heptyl, preferably methyl, ethyl, n-propyl, isopropyl, n-butyl, isobutyl, very particularly preferably isobutyl(2-methylpropyl).

Aldehydes of the formula (IV) to be used with preference are: acetaldehyde, valeraldehyde, isovaleraldehyde, pentanal, hexanal, heptanal, benzaldehyde, citral, citronellal. Aldehydes of the formula (IV) to be used with very particularly preference according to the invention are isovaleraldehyde and benzaldehyde, in particular isovaleraldehyde.

Within the context of a preferred embodiment, the present invention thus relates to a process for preparing and isolating 2-(2-methylpropyl)-4-hydroxy-4-methyltetrahydropyran of the formula (Ia) and of 2-(2-methylpropyl)-4-methyltetrahydropyran of the formula (IIa) (dihydrorose oxide)

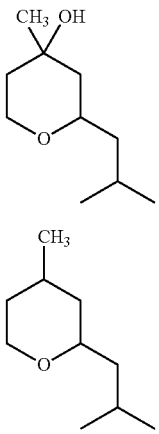

(I.a)

(II.a)

Preferably, in step a), the 3-methylbut-3-enol (III) and the aldehyde (IV) are used in a molar ratio of from about 1:2 to 2:1, particularly preferably from 0.7:1 to 2:1, in particular from 1:1 to 2:1. In a specific embodiment, in step a), the 3-methylbut-3-en-ol (III) and the aldehyde (IV) are used in a molar ratio of from 1:1 to 1.5:1.

According to the invention, the reaction in step a) takes place in the presence of an acidic catalyst. In principle, any acidic catalyst can be used for the reaction in step a), i.e. any substance which has Brönstedt or Lewis acidity. Examples of suitable catalysts are protic acids, such as hydrochloric acid, sulfuric acid, phosphoric acid, methanesulfonic acid and p-toluenesulfonic acid, acidic molecular elemental compounds, such as aluminum chloride, boron trifluoride, zinc chloride, phosphorus pentafluoride, arsenic trifluoride, tin tetrachloride, titanium tetrachloride and antimony pentafluoride; oxidic acidic solid bodies such as zeolites, silicates, aluminates, aluminosilicates, clays and acidic ion exchangers.

Preferably, the acidic catalyst used in step a) is selected from hydrochloric acid, sulfuric acid, methanesulfonic acid, p-toluenesulfonic acid and strongly acidic cation exchangers.

In a first variant, the reaction in step a) takes place in the presence of a Brönstedt acid, which is preferably selected from hydrochloric acid, sulfuric acid, methanesulfonic acid, p-toluenesulfonic acid. In this first variant, in step a), preference is given to using a solvent which is preferably selected from hydrocarbons and hydrocarbon mixtures. Suitable solvents are, for example, hexane, heptane, ligroin, petroleum ether, cyclohexane, decalin, toluene, xylene and mixtures thereof. In this first variant, the water content of the reaction mixture is at most 0.25% by weight, particularly preferably at most 2% by weight, based on the total weight of the reaction mixture. In the course of the reaction in step a), water can be formed, e.g. as a result of the dehydration of the process product of the formula (I) as possible side reaction. In order to nevertheless keep the water content low, the water formed can be distilled off together with the solvent used, the water can be at least partially separated off from the solvent by customary methods and then the solvent can be returned to reaction step a). Preferably, the catalyst in this first variant is used in an amount of from 0.05 to 5 mol %, particularly preferably from 0.1 to 4 mol %, based on the aldehyde (IV). Preferably, the reaction in step a) takes place in accordance with this first variant at a temperature in the range from 20 to 120° C., particularly preferably 40 to 110° C.

In a second variant, the reaction in step a) takes place in the presence of a strongly acidic cation exchanger. The term strongly acidic cation exchanger is understood here as meaning a cation exchanger in the $H^+$ form which has strongly acidic groups. The strongly acidic groups are usually sulfonic acid groups. The acidic groups are generally bonded to a polymer matrix, which can be e.g. gel-like and/or macroporous. A preferred embodiment of the process according to the invention is accordingly one wherein a strongly acidic cation exchanger having sulfonic acid groups is used. Suitable strongly acidic cation exchangers are described in WO 2010/133473 and WO 2011/154330, to which reference is made here in their entirety.

Of suitability for the use in step a) are strongly acidic ion exchangers (such as e.g. Amberlyst, Amberlite, Dowex, Lewatit, Purolite, Serdolit) which are based on polystyrene and which contain copolymers of styrene and divinylbenzene as carrier matrix with sulfonic acid groups in $H^+$-form, and ion exchanger groups functionalized with sulfonic acid groups ($-SO_3H$). The ion exchangers differ in the structure of their polymer backbones, and a distinction is made between gel-like and macroporous resins. In a specific embodiment, in step a), a perfluorinated polymeric ion exchange resin is used. Resins of this type are sold e.g. under the name Nafion® by DuPont. One example of such a perfluorinated polymeric ion exchange resin which may be mentioned is Nafion® NR-50.

Commercially available strongly acid cation exchangers suitable for the reaction in step a) are known, for example, under the trade names Lewatit® (Lanxess), Purolite® (The Purolite Company), Dowex® (Dow Chemical Company), Amberlite® (Rohm and Haas Company), Amberlyst™ (Rohm and Haas Company). Preferred strongly acidic cation exchangers are: Lewatit® K 1221, Lewatit® K 1461, Lewatit® K 2431, Lewatit® K 2620, Lewatit® K 2621, Lewatit® K 2629, Lewatit® K 2649, Amberlite® FPC 22, Amberlite® FPC 23, Amberlite® IR 120, Amberlyst™ 131, Amberlyst™ 15, Amberlyst™ 31, Amberlyst™ 35, Amberlyst™ 36, Amberlyst™ 39, Amberlyst™ 46, Amberlyst™ 70, Purolite® SGC650, Purolite® C100H, Purolite® C150H, Dowex® 50X8, Serdolit® red and Nation® NR-50.

The strongly acidic ion exchange resins are generally regenerated with hydrochloric acid and/or sulfuric acid.

In a specific embodiment, in step a), the 3-methylbut-3-enol (III) and the aldehyde (IV) are reacted in the presence of a strongly acidic cation exchanger and in the presence of water. In principle, the reaction mixture in step a) can already comprise small amounts of water which can be liberated by the dehydration of the process product of the formula (I) as a possible secondary reaction. According to one specific embodiment, water is also additionally added to the reaction mixture besides isoprenol (III) and the aldehyde of the formula (IV) and also any water from the reaction.

Usually, the reaction of isoprenol (III) with the aldehyde of the formula (IV) is carried out in the presence of about at least 10 mol % of added water, the amount of water referring to the amount of starting material isoprenol (III) or aldehyde (IV) used in each case in deficit or, in the case of the equimolar reaction of the two starting materials (III) and (IV), to the quantitative amount of one of the two.

Above the stated value, the amount of water can be chosen freely and is limited, if at all, only by processing or cost aspects and can be used entirely feasibly in a large, for example in a 10- to 100-fold excess or even more. Preferably, a mixture of isoprenol (III) and the aldehyde of the formula (IV), preferably isovaleraldehyde, is prepared with the amount of water to be added such that the added water remains dissolved in the mixture of isoprenol and the aldehyde, i.e. no two-phase system is present.

Usually, within the context of this embodiment of the process according to the invention, the starting materials isoprenol (III) and the aldehyde of the formula (IV) are reacted in the presence of at least 25 mol %, preferably of at least 50 mol %, even more preferably of at least 75 and even more preferably of at least 90 mol %, of added water, where the amount of water refers to the amount of the starting material isoprenol (III) or aldehyde (IV) used in each case in excess, or, in the case of the equimolar reaction of the two starting materials (III) and (IV), to the quantitative amount of one of the two.

Preferably, within the context of this embodiment of the process according to the invention, the starting materials isoprenol (III) and the aldehyde of the formula (IV) are reacted in the presence of up to about 1000 mol % of water, the amount of water referring to the amount of the starting material isoprenol (III) or aldehyde (IV) used in each case in deficit, or, in the case of the equimolar reaction of the two starting materials (III) and (IV), to the quantitative amount of one of the two.

Within the context of a preferred embodiment, the reaction to be carried out according to the invention is carried out such that it is carried out in the presence of an at least equimolar amount of added water, the amount of water referring to the amount of the starting material isoprenol (III) or aldehyde (IV) used in each case in deficit, or, in the case of the equimolar reaction of the two starting materials (III) and (IV), to the quantitative amount of one of the two. Consequently, the reaction according to the invention of isoprenol with the selected aldehyde of the formula (IV) is preferably carried out in the presence of 90 to 250 mol %, particularly preferably 90 to 230 mol %, even more preferably 90 to 200 mol % and most preferably in the presence of 90 to 180 mol %, of water, the amount of water referring to the amount of the starting material isoprenol (III) or aldehyde (IV) used in each case in deficit, or, in the case of the equimolar reaction of the two starting materials (III) and (IV), to the quantitative amount of one of the two.

For the reaction of isoprenol (III) with the aldehyde (IV) in step a), the specified starting materials and optionally the added water can be brought into contact with the acidic cation exchanger. Preferably, isoprenol (III), aldehyde (IV) and optionally the added water are used in the form of a mixture in step a). The specified starting materials, i.e. isoprenol (III) and the aldehyde (IV) and the water to be used in the above amount can be brought into contact with one another or mixed in any desired order.

The amount of strongly acidic cation exchanger in step a) is not critical and can be chosen freely within wide limits taking into consideration the economic and processing aspect. Accordingly, the reaction can be carried out either in the presence of catalytic amounts or in the presence of large excesses of the strongly acidic cation exchanger. Usually, the strongly acidic cation exchanger is used in an amount of from about 5 up to about 40% by weight, preferably in an amount of from about 20 to about 40% by weight and particularly preferably in an amount of from about 20 to about 30% by weight, in each case based on the sum of isoprenol (III) used and aldehyde of the formula (IV). Here, the data refer to the ready-to-use cation exchanger which is generally pretreated with water and accordingly can comprise amounts of up to about 70% by weight, preferably of about 30 to about 65% by weight and particularly preferably of about 40 to about 65% by weight of water. Particularly in the case of a discontinuous procedure, an additional addition of water when carrying out the process according to the invention may therefore be superfluous. The specified strongly acidic cation exchangers can be used in step a) either individually or else in the form of mixtures.

The reaction in step a) in the presence of a strongly acidic cation exchanger can, if desired, also additionally be carried out in the presence of a solvent that is inert under the reaction conditions. Suitable solvents are, for example, tert-butyl methyl ether, cyclohexane, decalin, hexane, heptane, ligroin, petroleum ether, toluene or xylene. The specified solvents can be used on their own or in the form of mixtures with one another. Preferably, the reaction in step a) is carried out in the presence of a strongly acidic cation exchanger without the addition of an organic solvent.

Preferably, the reaction of isoprenol (III) with the selected aldehyde (IV) in step a) is carried out in the presence of water and in the presence of a strongly acidic cation exchanger at a temperature in the range from 0 to 70° C., particularly preferably at a temperature in the range from 10 to 60° C. and in particular at a temperature in the range from 20 to 50° C. This is the temperature of the reaction mixture.

The reaction in step a) can be carried out discontinuously or continuously. In this connection, in the discontinuous case for example, the reaction can be undertaken such that a mixture of isoprenol (III), the aldehyde (IV), optionally water and optionally an organic solvent are introduced into a suitable reaction vessel, and the acidic catalyst is added. When the reaction is complete, the catalyst can then be separated off from the resulting reaction mixture by means of suitable separation methods. If, in step a), a Brönstedt acid, which is preferably selected from hydrochloric acid, sulfuric acid, methanesulfonic acid, p-toluenesulfonic acid, is used as catalyst, then the catalyst can be separated off by distillation e.g. after aqueous work-up, or by distillation directly. If, in step a) a strongly acidic cation exchanger is used as catalyst, then the catalyst can be separated of e.g. by filtration or by centrifugation.

Within the context of a preferred embodiment, the reaction of isoprenol (III) with the aldehyde (IV) in step a) is carried out continuously. For this, for example, a mixture of the starting materials isoprenol and aldehyde of the formula (III) that are to be reacted can be prepared with water, and this mixture can be brought into contact continuously with a strongly acidic cation exchanger. For this, the selected cation exchanger can be introduced for example into a suitable flow reactor, for example a stirred reactor with inlet and outlet or a tubular reactor, and the starting materials and the water can be discharged into this continuously and the reaction mixture can be discharged continuously. In this connection, the starting materials and the water can be introduced into the flow reactor, as desired, as individual components or else in the form of any mixture as described above.

The reaction mixture obtained in step a) of the process according to the invention comprises, besides the 2-substituted 4-hydroxy-4-methyltetrahydropyrans of the formula (I),

at least one of the compounds (V.1), (V.2) or (V.3) and at least one dioxane compound (VI)

where $R^1$ in the formulae (I), (V.1), (V.2), (V.3) and (VI) has the meaning given above. Preferably, $R^1$ is isobutyl. As a rule, the reaction mixture comprises a mixture of the compounds (V.1), (V.2) and (V.3).

The reaction mixture obtained in step a) of the process according to the invention can receive at least one further by-product, e.g. an acetal (VII)

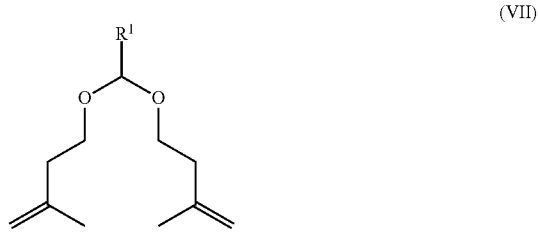

where $R^1$ has the meanings given above. Preferably, $R^1$ is isobutyl.

The reaction mixture obtained in step a) of the process according to the invention can comprise further components, such as unreacted 3-methylbut-3-en-1-ol (III), unreacted aldehyde (IV), water, organic solvent, etc.

Preferably, the reaction mixture obtained in step a) comprises the 2-substituted 4-hydroxy-4-methyltetrahydropyran of the formula (I) in an amount of from 50 to 90% by weight, particularly preferably 60 up to about 80% by weight, based on the total weight of the reaction mixture.

Preferably, the reaction mixture obtained in step a) comprises the compounds of the formulae (V.1), (V.2) and (V.3) in a total amount of from 5 to 20% by weight, particularly preferably 5 up to about 15% by weight, based on the total weight of the reaction mixture.

Preferably, the reaction mixture obtained in step a) comprises the dioxane compound of the formula (VI) in a total amount of from 5 to 20% by weight, particularly preferably 5 up to about 15% by weight, based on the total weight of the reaction mixture.

In a typical composition, the reaction mixture obtained in step a) comprises the following compounds, in each case based on the total weight of the reaction mixture:
Isovaleraldehyde: 0-5% by weight,
Isoprenol: 0-10% by weight,
Dihydropyran isomers (V.a-c): 5-15% by weight,
1,3-Dioxane (VI): 5-15% by weight,
Acetal (VII): 0-5% by weight,
trans-(I): 15-22% by weight,
cis-(I): 45-65% by weight,
Water: 2-10% by weight.

Preferably, the reaction mixture obtained in step a) comprises the 2-substituted 4-hydroxy-4-methyltetrahydropyrans of the formula (I) in the form of mixtures of the cis diastereomers of the formula cis-(I) and the trans diastereomers of the formula trans-(I)

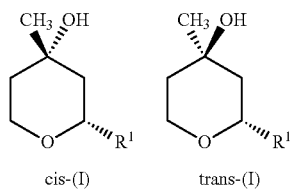

where the diastereomer ratio of the cis diastereomer cis-(1) to the trans diastereomer trans-(I) is preferably 65:35 to 95:5, particularly preferably 70:30 to 85:15, and $R^1$ has the meanings given above.

Preferably, the reaction mixture obtained in step a) comprises 2-isbutyl-4-hydroxy-4-methyltetrahydropyran in the form of mixtures of the cis diastereomer of the formula cis-(I.a) and of the trans diastereomer of the formula trans-(I.a)

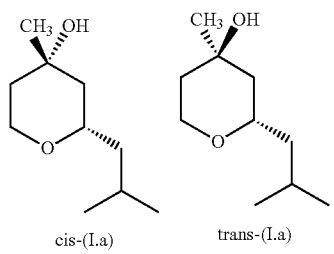

where the diastereomer ratio of the cis diastereomer cis-(I.a) to the trans diastereomer trans-(I.a) is preferably 65:35 to 95:5, particularly preferably 70:30 to 85:15.

On account of their specific odor properties, mixtures of this type are suitable to a particular extent for use as aroma chemicals, for example as a component with lily of the valley scent for producing fragrance compositions.

Step b)

The reaction product from step a) used for the separation in step b) comprises, based on the total weight, typically 45 to 65% by weight of the cis diastereomers cis-(I), 15 to 22% by weight of the trans diastereomers trans-(I), 10 to 30% by weight of compounds with a lower boiling point than the compounds (I), 1 to 3% by weight of compounds with a higher boiling point than the compounds (I). The reaction product from step a) is preferably essentially free from compounds which have a boiling point close to that of the stereoisomeric compounds (I). Within the context of the invention, essentially free from compounds which have a boiling point close to that of the stereoisomeric compounds (I) means that the reaction product from step a) comprises at most 1% by weight, particularly preferably at most 0.5% by weight, especially at most 0.1% by weight, of compounds which have a boiling point close to that of the stereoisomeric compounds (I).

Preferably, the reaction product from step a) used for the separation in step b) comprises 45 to 65% by weight of the cis-diastereomer of 2-isobutyl-4-hydroxy-4-methyltetrahydropyran of the formula cis-(I.a), 15 to 20% by weight of the trans-diastereomer of the formula trans-(I.a), 10 to 25% by weight of compounds with a lower boiling point than the compounds (I), 1 to 3% by weight of compounds with a higher boiling point than the compounds (I).

Preferably, in step b) of the process according to the invention, the reaction mixture from step a) is subjected to a distillative separation. Suitable devices for the distillative separation comprise distillation columns, such as tray columns, which can be equipped with bubble caps, sieve plates, sieve trays, packings, packing bodies, valves, side offtakes, etc., evaporators, such as thin-film evaporators, falling-film evaporators, forced-circulation evaporators, Sambay evaporators, etc. and combinations thereof.

The distillation columns can have separation-efficient internals, which are preferably selected from trays, structured packings, e.g. sheet-metal or fabric packings, such as Sulzer Mellapak®, Sulzer BX, Montz B1 or Montz A3 or Kühni Rombopak, or random beds of packing bodies, such as e.g. Dixon rings, Raschig rings, high-flow rings or Raschig superrings. Structured packings, preferably sheet-metal or fabric packings, with a specific surface area of from 100 to 750 $m^2/m^3$, in particular 250 to 500 $m^2/m^3$, have proven to be particularly useful. They permit high separation efficiencies coupled with low pressure drops.

Preferably, for the separation in step b), a device is used which comprises
a feed column with rectifying section positioned above the feed point, and stripping section positioned below the feed point,
an upper combining column communicating with the upper end of the rectifying section, and a lower combining column communicating with the lower end of the stripping section, and
a take-off column communicating with the upper combining column and the lower combining column.

Preferably, the separation in step b) takes place by
i) introducing the reaction product from step a) into a feed column with rectifying section positioned above the feed point and stripping section positioned below the feed point, ii) providing an upper combining column communicating with the upper end of the rectifying section with condenser at the upper end of the column, and a lower combining column communicating with the lower end of the stripping section with heater at the lower end of the column, iii) providing a take-off column communicating with the upper combining column and the lower combining column and having at least one side take-off, iv) drawing off from the take-off column at the top or in the upper region compounds with a lower boiling point than the 2-substituted 4-hydroxy-4-methyltetrahydropyrans (I), drawing off as at least one side take-off at least some of the 2-substituted 4-hydroxy-4-methyltetrahydropyrans (I) and drawing off at the bottom or in the lower region of the lower combining column the 2-substituted 4-hydroxy-4-methyltetrahydropyrans (I) that are not drawn off as side take-off and the compounds with a higher boiling point than the 2-substituted 4-hydroxy-4-methyltetrahydropyrans (I).

In a preferred embodiment, the take-off removed from the take-off column at the top or in the upper region comprises:
at least some or all of the compounds (V.1), (V.2) and (V.3) present in the reaction product from step a),
at least some or all of the dioxane compound (VI) present in the reaction product from step a),
if present, unreacted 3-methylbut-3-en-1-ol of the formula (III),
if present, unreacted aldehyde (IV),
small amounts or no 4-hydroxy-4-methyltetrahydropyrans (I),
water.

In a particularly preferred embodiment, 3-methylbut-3-en-1-ol of the formula (III) and isovaleraldehyde (IV) are used for the reaction in step a). Then, the take-off removed from the take-off column at the top or in the upper region comprises:
at least some or all of the compounds (V.1), (V.2) and (V.3), in which $R^1$ is isobutyl, present in the reaction product from step a),
at least some or all of the dioxane compound (VI), in which $R^1$ is isobutyl, present in the reaction product from step a),
if present, unreacted 3-methylbut-3-en-1-ol of the formula (III),
if present, unreacted isovaleraldehyde (IV),
small amounts or no 2-(2-methylpropyl)-4-hydroxy-4-methyltetrahydropyran of the formula (Ia),
water.

The top product obtained in this way can be subjected to a phase separation to separate off the majority of the water. Apart from such a phase separation, the top product obtained in this way can generally be used without further work-up for the hydrogenation in step c). If desired, the top product can be subjected to a further workup for separating off at least some of the components different from the compounds (V.1), (V.2), (V.3) and (VI). For the purpose, the top product can be subjected e.g. to a further distillative separation.

In a preferred embodiment, one side stream is drawn off from the take-off column or two side streams are drawn off from the take-off column. In a specific embodiment, only one side stream is drawn off from the take-off column.

If, in step b), two or more take-offs are removed which comprise 2-substituted 4-hydroxy-4-methyltetrahydropyrans (I), e.g. two different side take-offs or one side take-off and one bottom take-off, then these generally differ with regard to the composition of the stereoisomers. Consequently, the isolation of a fraction enriched in cis diastereomers compared with the reaction product from step a) and of a fraction enriched in trans diastereomer is possible. In the event of adequate separation efficiency of the distillation device used, at least one of the diastereomers can, if desired, be obtained in pure form.

The feed column, take-off column, upper combining column and lower combining column can be discrete structural elements or be configured as a section or chamber of a distillation column which combines a number of functions. The expression "communicating columns" means that there is an exchange both of rising vapors and also of discharging condensate between them.

In one preferred embodiment of the process according to the invention, the distillative separation in step b) takes place in an arrangement of distillation columns which comprises a dividing-wall column or an interconnection of at least two thermally coupled conventional distillation columns.

Dividing-wall columns are special distillation columns with at least one feed point and at least three removal points, in which the so-called rectification region is located between evaporator and condenser, in which some of the condensate formed in the condenser moves downwards in liquid form as runback countercurrently to the vapors rising from the evaporation apparatus and which comprises, in one part region of the column below and/or above the feed point, at least one dividing device (dividing wall), acting in a longitudinal direction, to prevent crossmixing of the liquid stream and/or vapor stream, and which thus permit distillative separation of substance mixtures. The basic principle of the dividing-wall columns has been known for a long time and is described for example in U.S. Pat. No. 2,471,134, in ER-A-0 122 367 or in G. Kaibel, Chem. Eng. Technol. vol. 10, 1987, pages 92 to 98.

The general basic construction of a dividing-wall column comprises at least one side feed point on one side of the dividing wall and at least three removal points, at least one of which is on the other side of the dividing wall. Since in this type of construction, crossmixing of liquid stream and/or vapor stream is prevented in the region of the dividing wall, it is possible to obtain the side products in pure form. This generally reduces the number of distillation columns required overall for the separation of multicomponent mixtures. Moreover, capital costs and also energy can be saved when using dividing-wall columns compared with a simple serial arrangement of two conventional distillation columns (see M. Knott, Process Engineering, vol. 2, 1993, February, pages 33 to 34).

Within the context of the invention, conventional distillation columns is the term used to refer to all distillation columns which do not comprise a dividing wall. In thermally coupled conventional distillation columns, mass and energy streams are mutually exchanged. Consequently, a significant saving of energy is possible compared to a simple serial arrangement of conventional distillation columns. As an alternative to the dividing-wall column, preference is given to an arrangement of two thermally coupled distillation columns. An overview of various arrangements is given, for example, in G. Kaibel et al., Chem.-Ing.-Tech., vol. 61, 1989, pages 16 to 25 and G. Kaibel et al., Gas Separation & Purification, vol. 4, 1990, June, pages 109 to 114.

In a first preferred embodiment, a distillation column with a thermally coupled precolumn, i.e. the take-off column, the upper combining column and the lower combining column are designed as a single-section distillation column, and the feed column is designed as a precolumn to the distillation column, is used. In a second preferred embodiment, a distillation column with a thermally coupled postcolumn, i.e. the feed column, the upper combining column and the lower combining column are designed as a single-section distillation column and the take-off column is designed as a postcolumn to the distillation column, is used. Distillation columns with connected auxiliary columns are known and described e.g. in Chem. Eng. Res. Des., Part A: Trans IChemE, March 1992, pp. 118-132, "The design and optimisation of fully thermally coupled distillation columns".

It has proven to be favorable to remove at least some of the compounds with a lower boiling point than the 2-substituted 4-hydroxy-4-methyltetrahydropyrans (I) from the reaction product from step a) prior to introducing it into the feed column. In one specific embodiment, therefore, an arrangement of distillation columns is used for the distillative separation of the reaction product from step a) which comprises an upstream conventional distillation column and a downstream dividing-wall column or a downstream interconnection of two thermally coupled conventional distillation columns.

Preferably, for the distillative separation in step b),
b1) the reaction mixture from step a) is subjected firstly to a separation in a conventional distillation column, where a first top product is obtained which is enriched in the compounds (V.1), (V.2) and (V.3) and the dioxane compound (VI) and comprises essentially no compounds of the general formula (I), and a first bottom product is obtained which is depleted in the compounds (V.1), (V.2) and (V.3) and the dioxane compound (VI) and comprises the majority of the compounds of the general formula (I),
b2) the first bottom product from step b1) is subjected to a separation in a dividing-wall column or in an interconnection of two thermally coupled conventional distillation columns, where a second top product is obtained which comprises the compounds (V.1), (V.2) and (VI) not present in the first top product, and also optionally small amounts of the compounds of the general formula (I), a side stream is obtained which consists essentially of compound of the general formula (I), and a second bottom product is obtained which comprises the compounds of the general formula (I) which are not present in the top product and are not present in the side stream.

Preferably, in the aforementioned embodiment, in the compounds of the formulae (I), (V.1), (V.2), (V.3) and (VI), $R^1$ is also isobutyl.

The expression according to which the first top product comprises essentially no compounds of the general formula (I) means that the fraction of compounds of the general formula (I) in the first top product is at most 5% by weight, particularly preferably at most 2% by weight, especially at most 1% by weight, specifically at most 0.1% by weight, based on the total weight of the first top product. In a specific embodiment, the first top product comprises no compounds of the general formula (I).

The second top product can comprise for example 0.1 to 25% by weight, particularly preferably 0.2 to 20% by weight, in particular 0.3 to 15% by weight, specifically 0.5 to 10% by weight, of compounds of the general formula (I), based on the total weight of the second top product.

In a specific embodiment, the side stream consists only of compounds of the general formula (I).

In a specific embodiment, the second bottom product consists only of compounds of the general formula (I). Alternatively, the second bottom product can comprise compounds which have a higher boiling point than the compounds of the general formula (I).

Preferably, according to this embodiment, the first top product (in particular the organic phase of the first top product depleted in water) and/or the second top product is used for the hydrogenation is step c). Here, it is unimportant if the second top product still comprises small amounts of the compounds of the general formula (I) since these generally pass through the hydrogenation in step c) unchanged and can then, if desired, be separated off and put to good use.

As a rule, in this embodiment, the side product and the second bottom product are different with regard to the fraction of the stereoisomers of the compounds of the formula (I).

Step c)

The hydrogenation of the compounds (V.1), (V.2) and (V.3) to give the corresponding 2-substituted 4-methyltetrahydropyrans (II) can be carried out in a conventional manner per se with hydrogenation catalysts from the prior art.

The hydrogenation can take place catalytically either in the gas phase or liquid phase. Preferably, the hydrogenation in step c) of the process according to the invention is carried out in liquid phase in the presence of a heterogeneous hydrogenation catalyst and a hydrogen-containing gas.

Suitable hydrogenation catalysts are in principle all homogeneous and heterogeneous catalysts suitable for the hydrogenation of unsaturated organic compounds. These include e.g. metals, metal oxides, metal compounds or mixtures thereof. Suitable hydrogenation catalysts comprise preferably at least one transition metal, preferably from subgroups I and VI to VIII of the Periodic Table of the Elements. These include preferably Cu, Cr, Mo, Mn, Re, W, Fe, Rh, Co, Ni, Pd, Pt, Ru, Zn or mixtures thereof.

The catalysts can consist just of the active components, or the active components can be applied to supports. Suitable support materials are e.g. $Al_2O_3$, $SiO_2$, $ZrO_2$, $TiO_2$, activated carbon, ZnO, BaO and MgO or mixtures thereof.

To increase the catalytic activity, it is possible to use Fe, Co and preferably Ni, also in the form of the Raney catalysts or as metal sponge with a very large surface area.

Preferably, palladium on carbon or platinum on carbon is used for the hydrogenation in step c) of the process according to the invention. Furthermore, Raney nickel or Raney cobalt can be used advantageously.

Other suitable catalysts comprise e.g. 80 to 100% by weight of nickel and/or cobalt and up to 20% by weight of activating metals such as copper and/or chromium. Such catalysts are used particularly advantageously as supported catalysts. The content of catalytically active metals of such supported catalysts is generally 5 to 80% by weight, based on the sum of catalytically active metals and support.

The catalysts can be used for the hydrogenation in step c) as moldings. Examples comprise catalyst extrudates, such as strands, ribbed strands and other extrudate forms, coated catalysts, tablets, rings, beads, grit, etc.

Preferably, the hydrogenation in step c) is carried out at a temperature of from 20 to 200° C., preferably 40 to 150° C., in particular 50 to 120° C.

If the reaction is carried out in the gas phase, pressures of from 1 to 100 bar, preferably 1.1 to 50 bar, have proven useful.

If the reaction is carried out in the liquid phase, the pressure is preferably in a range from 2 to 500 bar, particularly preferably from 3 to 300 bar, in particular from 4 to 250 bar, specifically from 5 to 200 bar.

The hydrogenation in step c) can be carried out in one reactor or a plurality of serially connected reactors. The hydrogenation can take place discontinuously or continuously. For the discontinuous hydrogenation, e.g. a pressurized vessel can be used. Suitable pressurized vessels are e.g. autoclaves equipped with a device for heating and for stirring the reactor contents. Preferably, the hydrogenation takes place in the liquid phase via a fixed bed, preferably in liquid-phase mode or trickle mode or in the form of a suspension catalysis.

The hydrogenation can take place with or without the addition of a solvent. Suitable solvents are alcohols, ethers, hydrocarbons, such as, for example, methanol, ethanol, isopropanol, dioxane, tetrahydrofuran, n-pentane, hexane, cyclohexane, toluene, etc. Preferably, the hydrogenation in step c) takes place without the addition of a solvent.

For the hydrogenation in step c), the fraction which comprises at least one of the compounds (V.1), (V.2) or (V.3) and at least one dioxane compound (VI) can be brought into contact with a hydrogen-containing gas and a hydrogenation catalyst. Suitable hydrogen-containing gases are selected from hydrogen and mixtures of hydrogen with at least one inert gas. Suitable inert gases are e.g. nitrogen or argon. For the hydrogenation in step c), preference is given to using hydrogen in undiluted form, usually in a purity of about 99.9% by volume.

As a result of the hydrogenation in step c), the compounds (V.1), (V.2) and (V.3) present in the starting mixture are converted to 2-substituted 4-methyltetrahydropyrans (II). Preferably, the starting mixture used for the hydrogenation comprises compounds of the formula (V.1), (V.2) and (V.3), where the radical $R^1$ is isobutyl. Then, as a result of the hydrogenation in step c), the compounds (V.1), (V.2) and (V.3) present in the starting mixture are converted to 2-isobutyl-4-methyltetrahydropyran (II) (dihydrorose oxide).

Preferably, in step c), a hydrogenation product is obtained where the diastereomer ratio of the cis diastereomer of 2-substituted 4-methyltetrahydropyran (II) to the trans diastereomer is in a range from 60:40 to 95:5, preferably from 65:35 to 90:10. Particularly preferably, in step c), a hydrogenation product is obtained where the diastereomer ratio of the cis diastereomer of 2-isobutyl-4-methyltetrahydropyran (II) to the trans diastereomer is in a range from 60:40 to 95:5, preferably from 65:35 to 90:10.

On account of their particular odor properties, mixtures of this type are suitable to a particular degree for use as aroma chemicals, for example as component with rose scent-like character for producing fragrance compositions.

Step d)

From the hydrogenation product obtained in step c) it is in principle possible to isolate a fraction enriched in 2-substituted 4-methyltetrahydropyrans (II) and a fraction enriched in the at least one dioxane compound (VI) by customary purification methods known to the person skilled in the art.

Preferably, the hydrogenation product obtained in step c) is subjected to a distillative separation. Suitable devices for the distillative separation comprise distillation columns, such as tray columns, which can be equipped with bubble caps, perforated plates, perforated trays, packings, packing bodies, valves, side takeoffs, etc., evaporators, such as thin-film evaporators, falling-film evaporators, forced-circulation evaporators, Sambay evaporators, etc. and combinations thereof.

Preferably, the hydrogenation product obtained in step c) is subjected in step d) to a distillative separation in at least one distillation column which is provided with separation-efficient internals.

Preferably, in step d), from the hydrogenation product obtained in step c) is isolated a fraction enriched in 2-substituted 4-methyltetrahydropyrans (II), where the diastereomer ratio of the cis diastereomer to the trans diastereomer is in a range from 60:40 to 100:0, preferably from 65:35 to 90:10.

Particular preferably, in step d), from the hydrogenation product obtained in step c) is isolated a fraction enriched in 2-isobutyl-4-methyltetrahydropyran (II), where the diastereomer ratio of the cis diastereomer to the trans diastereomer is in a range from 60:40 to 100:0, preferably from 65:35 to 90:10.

Preferably, in step d), from the hydrogenation product obtained in step c) is isolated a fraction enriched in 2-substituted 4-methyltetrahydropyrans (II) which has a content of dioxane compounds of the general formula (VI)

in which $R^1$ has the meanings given above and is in particular isobutyl,
of at most 2% by weight, particularly preferably of at most 1% by weight, very particularly preferably of at most 0.1% by weight.

The compositions according to the invention and the compositions obtainable by the process according to the invention are particularly advantageously suitable as fragrance or for the provision of a fragrance.

The compositions according to the invention can be diluted as desired for the use as fragrance with at least one solvent customary in this field of application. By way of example, the following suitable solvents may be mentioned: ethanol, dipropylene glycol or ethers thereof, phthalates, propylene glycols, or carbonates of diols, preferably ethanol. Water is also suitable as solvent for diluting the fragrance compositions according to the invention and can advantageously be used together with suitable emulsifiers.

On account of the structural and chemical similarity of the components, the fragrances obtained by the process according to the invention have a high stability and durability. The isomer mixtures of 2-(2-methylpropyl)-4-hydroxy-4-methyltetrahydropyran of the formula (Ia) obtainable by the process according to the invention are characterized by a pleasant lily of the valley odor. The isomer mixtures of 2-(2-methylpropyl)-4-methyltetrahydropyran of the formula (IIa) (dihydrorose oxide) obtainable by the process according to the invention are characterized by a pleasant rose-like character.

The fragrances obtained by the process according to the invention are suitable for incorporation into cosmetic compositions, and also utility and consumer articles and/or compositions as described in more detail below, it being possible to incorporate the fragrances into said articles or else apply them thereto. Within the context of the entire present invention, an organoleptically effective amount is to be understood in particular as meaning an amount which suffices, upon application as intended, to bring about a scent impression for the user or consumer.

Suitable cosmetic compositions are all customary cosmetic compositions. These are preferably perfume, Eau de Toilette, deodorants, soap, shower gel, bathing gel, creams, lotions, sunscreens, compositions for cleansing and caring for the hair, such as hair shampoo, conditioner, hair gel, hair setting compositions in the form of liquids or foams and other cleansing or care compositions for the hair, compositions for decorative application on the human body, such as cosmetic sticks, for example lipsticks, lip care sticks, concealing sticks (concealers), blushers, eye shadow pencils, lip liner pencils, eyeliner pencils, eyebrow pencils, correction pencils, sunscreen sticks, antiacne sticks and comparable products, and also nail varnishes and other products for nail care.

The fragrances obtained by the process according to the invention are specifically suitable for use in perfumes, e.g. as Eau de Toilette, shower gels, bathing gels and body deodorants.

They are also suitable for aromatizing consumer or utility articles into which they are incorporated and/or onto which they are applied and to which they thereby impart a pleasant fresh green accent. Examples of consumer or utility articles are: room air deodorants (air care), cleaning compositions or care compositions for textiles (specifically detergents, fabric softeners), textile treatment compositions such as, for example, ironing aids, scouring agents, cleaners, care compositions for treating surfaces, for example furniture, floors, kitchen appliances, glass panes and windows and also monitors, bleaches, toilet blocks, limescale removers, fertilizers, construction materials, mold removers, disinfectants, products for car and vehicle care and the like.

The examples below serve to illustrate the invention without limiting it in any way.

EXAMPLES

Gas chromatographic analyses were carried out according to the following method:
Column: DB WAX 30 m×0.32 mm;
FD 0.25 µm;
Injector temperature: 200° C.; detector temperature 280° C.;
Temperature program: Starting temp.: 50° C., at 3° C./min to 170° C.,
at 20° C./min to 230° C., 7 min isotherm;
Retention times: Isovaleraldehyde $t_R$=3.7 min
cis-Dihydrorose oxide $t_R$=8.4 min
trans-Dihydrorose oxide $t_R$=9.6 min
4,4-Dimethyl-2-isobutyl-1,3-dioxane $t_R$=11.9 min
Concentrations of the resulting crude products (% by weight) were ascertained by GC analysis with an internal standard.

Example 1

Hydrogenation of the Isomeric Dihydropyrans V.1a-V.1c)

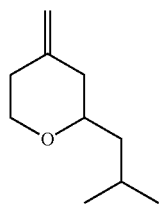

(V.1a)

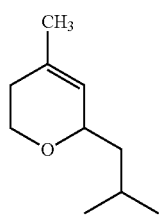

(V.1b)

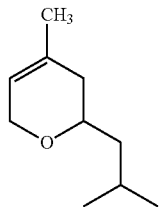

(V.1c)

A mixture of the isomeric dihydropyrans V.1a to V.1c (100 g, 0.65 mol) was introduced into an autoclave (maximum fill level 180 ml) at room temperature and treated with palladium on carbon (5.8% Pd, 50% water-moist). After closing the autoclave, it was flushed three times with nitrogen (20 bar), hydrogen was injected to a pressure of 100 bar, the stirrer was switched on (700 rpm) and the autoclave was heated to 120° C. At 120° C., 200 bar of hydrogen were injected and stirring was carried out for a further 15 h at this pressure. After cooling to room temperature and decompression, the product filtered through a suction filter (Por4=nominal width of the pores 10-16 µm). This gave the crude product (92 g) with the following composition: cis-dihydrorose oxide: 73.4 GC area % ($t_R$=8.7 min); trans-dihydrorose oxide: 24.1 GC area % ($t_R$=9.9 min). After subsequent distillative work-up over a 40 cm-long packed column (metal raschig rings) and a pressure of 31 mbar, the product was obtained at a transition temperature of 73 to 74° C. with a purity of 99.7 GC area % and an isomer ratio of cis-dihydrorose oxide:trans-dihydrorose oxide=3/1.

Example 2

A mixture of isovaleraldehyde (112.5 g, 1.31 mol), isoprenol (125 g, 1.45 mol) and 12.5 g of water was reacted in the presence of 50 g of the strongly acidic cation exchanger Amberlyst® 131, as described in example 1 of WO 2011/154330. The resulting reaction mixture was subjected to a distillative separation in an arrangement consisting of a conventional distillation column and a dividing-wall column.

A mixture (total=150 g, representative top takeoff of the dividing-wall column) of isovaleraldehyde (0.4%), isoprenol (0.8%), the isomeric dihydropyrans V.1a to V.1c (43.2%), 4,4-dimethyl-2-isobutyl-1,3-dioxane (42.0%), isoprenyl ether from pyranol (1.9%) and the isomeric pyranols cis-(I.a) and trans-(I.a) (7.5%) was introduced into an autoclave (maximum filling 180 ml) and treated with palladium on carbon (5.8% Pd, 50% water-moist). After closing the autoclave, it was flushed three times with nitrogen (20 bar), hydrogen was injected to a pressure of 150 bar, the stirrer was switched on (700 rpm) and the autoclave was heated to 120° C. At 120° C., 200 bar of hydrogen were injected and stirring was carried out for a further 15 h at this pressure. After cooling to room temperature and decompression to 0 bar, the product was filtered through a suction filter (Por4=nominal width of the pores 10-16 µm). This gave the crude product (140 g) with the following composition: isovaleraldehyde: 0.4 GC area % ($t_R$=3.7 min); cis-dihydrorose oxide: 37.6 GC area % ($t_R$=8.4 min); trans-dihydrorose oxide: 10.3 GC area % ($t_R$=9.6 min); dioxane: 36.9 GC area % ($t_R$=11.9 min); IMTP: 3.1 GC area % ($t_R$=27.0 min); pyranol: 7.1 GC area % ($t_R$=28.2 min). After subsequent distillative purification over a 85 cm-long packed column (metal raschig rings) and a pressure of 20 mbar, the top product was obtained at a transition temperature of 48° C. with the following composition: cis-dihydrorose oxide 1: 91.0 GC area % ($t_R$=8.4 min); trans-dihydrorose oxide 2: 7.1 area % ($t_R$=9.6 min); dioxane: 0.6 GC area % ($t_R$=11.9 min); 2-methyl-2,4-butanediol 0.5 GC area % ($t_R$=26.8 min).

Example 3

A mixture of isovaleraldehyde (112.5 g, 1.31 mol), isoprenol (125 g, 1.45 mol) and 12.5 g of water was reacted in the presence of 50 g of the strongly acidic cation exchanger Amberlyst® 131, as described in example 1 of WO 2011/154330. The resulting reaction mixture was subjected to a distillative separation in an arrangement consisting of a conventional distillation column and a dividing-wall column.

A mixture of the top takeoffs of the above-mentioned columns (total amount of the mixture: 100 g) of isovaleraldehyde (12.1%), isoprenol (10.7%), the isomeric dihydropyrans V.1a-V.1c (50.3%), 4,4-dimethyl-2-isobutyl-1,3-dioxane (20.8%) and the isomeric pyranols cis-(I.a) and trans-(I.a) (6%) was introduced into an autoclave (maximum filling 180 ml) and treated with Raney nickel catalyst (water-moist; 1 g). After closing the autoclave, it was flushed three times with nitrogen (20 bar), the stirrer was switched on (700 rpm), hydrogen was injected to a pressure of 5 bar, and the autoclave was heated to 150° C. At 150° C., 10 bar of hydrogen were injected and stirring was carried out for a further 20 h at this pressure. After cooling to room temperature and decompression to 0 bar, the product was filtered through a suction filter (nominal width of the pores 10-16 μm). This gave the crude product with the following composition: isovaleraldehyde: 0.6 GC % by weight ($t_R$=3.7 min); cis-dihydrorose oxide: 22.1 GC % by weight ($t_R$=8.0 min); isoamyl alcohol: 22.5 GC area % ($t_R$=8.8 min); trans-dihydrorose oxide: 21.6 GC % by weight ($t_R$=9.2 min); dihydropyrans V.1a-V.1c: 0.3 GC % by weight ($t_R$=9.4, 11.1, 11.8 min); dioxane: 19.8 GC % by weight ($t_R$=11.5 min); pyranol cis-(I.a) and trans-(I.a): 5.9 GC % by weight ($t_R$=27.3, 28.7 min).

The distillative work-up of the crude product can be effected as in example 1 or 2.

Example 4

A mixture of isovaleraldehyde (112.5 g, 1.31 mol), isoprenol (125 g, 1.45 mol) and 12.5 g of water was reacted in the presence of 50 g of the strongly acidic cation exchanger Amberlyst® 131, as described in example 1 of WO 2011/154330. The resulting reaction mixture was subjected to a distillative separation in an arrangement consisting of a conventional distillation column and a dividing-wall column.

A mixture of the top takeoffs of the above-mentioned columns (total amount of the mixture: 50 g) of isovaleraldehyde (4.5%), isoprenol (11.3%), the isomeric dihydropyrans V.1a-V.1c (35.3%), 4,4-dimethyl-2-isobutyl-1,3-dioxane (39.8%) and the isomeric pyranols cis-(I.a) and trans-(I.a) (2.5%) was introduced into an autoclave (maximum filling 180 ml) and treated with palladium on carbon (5% Pd on C, 50% water-moist; 2 g) and with methanol (100 ml). After closing the autoclave, it was flushed three times with nitrogen (20 bar), the stirrer was switched on (700 rpm), hydrogen was injected to a pressure of 5 bar and the autoclave was heated to 85° C. At 85° C., 10 bar of hydrogen was injected and stirring was carried out for a further 15 h at this pressure. After cooling to room temperature and decompression to 0 bar, the product was filtered through a suction filter (nominal width of the pores 10-16 μm). This gave the crude product with the following composition: methanol: 42.0 GC area % ($t_R$=3.4 min); 1,1-dimethoxy-3-methylbutane: 10.4 GC area % (4.6 min); isovaleraldehyde: 0.5 GC % by weight ($t_R$=3.7 min); cis-dihydrorose oxide: 9.8 GC % by weight ($t_R$=8.0 min); isoamyl alcohol: 2.1 GC area % ($t_R$=8.7 min); trans-dihydrorose oxide: 2.7 GC % by weight ($t_R$=9.1 min); dioxane: 8.0 GC % by weight ($t_R$=11.4 min); pyranol cis-(I.a) and trans-(I.a): 1.0 GC % by weight ($t_R$=27.3, 28.9 min).

The distillative work-up of the crude product can be effected as in example 1 or 2.

The invention claimed is:
1. A process for preparing 2-substituted 4-hydroxy-4-methyltetrahydropyrans of formula (I) and of 2-substituted 4-methyltetrahydropyrans of formula (II)

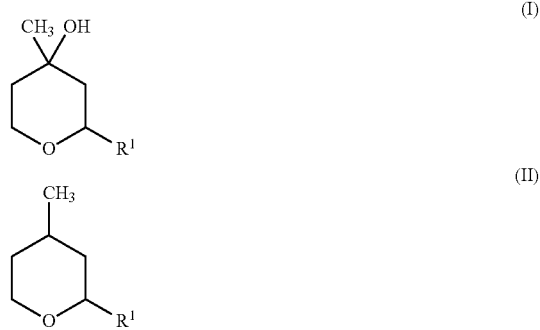

in which
R$^1$ is straight-chain or branched $C_1$-$C_{12}$-alkyl, straight-chain or branched $C_2$-$C_{12}$-alkenyl, unsubstituted or $C_1$-$C_{12}$-alkyl- and/or $C_1$-$C_{12}$-alkoxy-substituted cycloalkyl having in total 3 to 20 carbon atoms or unsubstituted or $C_1$-$C_{12}$-alkyl- and/or $C_1$-$C_{12}$-alkoxy-substituted aryl having in total 6 to 20 carbon atoms,
which comprises reacting
a) 3-methylbut-3-en-1-ol of formula (III)

with an aldehyde of formula (IV)

in the presence of an acidic catalyst, giving a reaction mixture which comprises at least one 2-substituted 4-hydroxy-4-methyltetrahydropyran of formula (I), at least one of the compounds (V.1), (V.2) or (V.3) and at least one dioxane compound (VI)

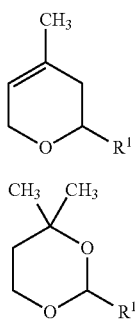

(V.3)

(VI)

b) subjecting the reaction product from step a) to a separation, giving a fraction comprising 2-substituted 4-hydroxy-4-methyltetrahydropyrans of formula (I) and a fraction which comprises at least one of the compounds (V.1), (V.2) or (V.3) and at least one dioxane compound (VI), c) subjecting the fraction which comprises at least one of the compounds (V.1), (V.2) or (V.3) and at least one dioxane compound (VI) to hydrogenation, d) isolating a fraction comprising 2-substituted 4-methyltetrahydropyrans (II) and a fraction comprising the at least one dioxane compound (VI) from the hydrogenation product obtained in step c).

2. The process according to claim 1, where $R^1$ is isobutyl or phenyl.

3. The process according to claim 1, in which the reaction in step a) takes place in the presence of an acidic catalyst which is selected from the group consisting of hydrochloric acid, sulfuric acid, methanesulfonic acid, p-toluenesulfonic acid and strongly acidic cation exchangers.

4. The process according to claim 3, in which the reaction in step a) is carried out in the presence of a strongly acidic cation exchanger.

5. The process according to claim 4, in which the reaction in step a) is carried out in the presence of a strongly acidic cation exchanger and in the presence of added water.

6. The process according to claim 1, where, in step b), the reaction product from step a) is subjected to a distillative separation.

7. The process according to claim 6, where, for the separation in step b), a device is used which comprises
a feed column with rectifying section positioned above the feed point, and stripping section positioned below the feed point,
an upper combining column communicating with the upper end of the rectifying section, and a lower combining column communicating with the lower end of the stripping section, and
a take-off column communicating with the upper combining column and the lower combining column.

8. The process according to claim 6, where the distillative separation takes place in an arrangement of distillation columns which comprises a dividing-wall column or an interconnection of at least two thermally coupled conventional distillation columns.

9. The process according to claim 6, where, for the distillative separation of the reaction product from step a), an arrangement of distillation columns is used which comprises an upstream conventional distillation column and a downstream dividing-wall column or a downstream interconnection of two thermally coupled conventional distillation columns.

10. The process according to claim 9, where, for the distillative separation in step b),
the reaction mixture from step a) is subjected firstly to a separation in a conventional distillation column, where a first top product is obtained which comprises the compounds (V.1), (V.2) and (V.3) and the dioxane compound (VI) and comprises essentially no compounds of formula (I), and a first bottom product is obtained which comprises compounds of formula (I), and
the first bottom product is subjected to a separation in a dividing-wall column or in an interconnection of two thermally coupled conventional distillation columns, where a second top product is obtained which comprises the compounds (V.1), (V.2), (V.3) and (VI) not present in the first top product, and also optionally small amounts of the compounds of formula (I), a side stream is obtained which consists essentially of compound of formula (I), and a second bottom product is obtained which comprises the compounds of formula (I) which are not present in the top product and are not present in the side stream.

11. The process according to claim 10, where, in the compounds of formulae (I), (V.1), (V.2), (V.3) and (VI), $R^1$ is isobutyl.

12. The process according to claim 10, where the first top product and/or the second top product are used for the hydrogenation in step c).

13. The process according to claim 10, where the side stream and the second bottom product differ with regard to the fraction of stereoisomers of the compounds of formula (I).

14. The process according to claim 1, where the hydrogenation in step c) takes place in the presence of a hydrogenation catalyst which is selected from homogeneous and heterogeneous catalysts which comprise at least one metal component selected from metals, metal compounds or mixtures thereof.

15. The process according to claim 14, where the hydrogenation catalyst is palladium on carbon, platinum on carbon, Raney nickel or Raney cobalt.

16. The process according to claim 1, where, in step d), the hydrogenation product obtained in step c) is subjected to a distillative separation.

17. The process according to claim 1, where, in step d), a fraction comprising 2-substituted 4-methyltetrahydropyrans (II) is isolated from the hydrogenation product obtained in step c), where the diastereomer ratio of the cis-diastereomer to the trans-diastereomer is in a range from 60:40 to 100:0.

18. The process according to claim 1, where, in step d), a fraction comprising 2-substituted 4-methyltetrahydropyrans (II) is isolated from the hydrogenation product obtained in step c), said fraction having a content of dioxane compounds of formula (VI)

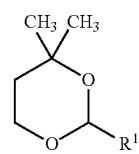

(VI)

which is of at most 2% by weight.

19. The process according to claim 18, where, in step d), a fraction comprising 2-isopropyl-4-methyltetrahydropyran (II) is isolated.

20. The process according to claim 18, wherein $R^1$ is butyl and said fraction having a content of dioxane compounds of formula (VI)
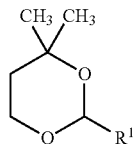
(VI)
is of at most 1% by weight.
21. The process according to claim 14, wherein the metal compound is a metal oxide.
* * * * *